United States Patent [19]

Seki et al.

[11] Patent Number: 5,364,991
[45] Date of Patent: Nov. 15, 1994

[54] PREPARATION OF 1,1,1,4,4,4-HEXAFLUOROBUTANE

[75] Inventors: Eiji Seki; Hirokazu Aoyama; Tatsuo Nakada; Satoshi Koyama, all of Osaka, Japan

[73] Assignee: Daikin Industries, Ltd., Osaka, Japan

[21] Appl. No.: 90,044

[22] PCT Filed: Nov. 24, 1992

[86] PCT No.: PCT/JP92/01529
§ 371 Date: Jul. 20, 1993
§ 102(e) Date: Jul. 20, 1993

[87] PCT Pub. No.: WO93/10067
PCT Pub. Date: May 27, 1993

[30] Foreign Application Priority Data

Nov. 22, 1991 [JP] Japan .................................. 3-307597
Dec. 4, 1991 [JP] Japan .................................. 3-320324

[51] Int. Cl.$^5$ .............................................. C07C 19/08
[52] U.S. Cl. ........................................ 570/175; 570/176
[58] Field of Search ........................ 570/160, 176, 175

[56] References Cited

U.S. PATENT DOCUMENTS 5,146,019 9/1992 Bielefeldt et al. ................... 570/160
5,210,340 5/1993 Bielefeldt et al. .

FOREIGN PATENT DOCUMENTS 0301346 2/1989 European Pat. Off. .
0324478 7/1989 European Pat. Off. ............ 570/178
0442087 8/1991 European Pat. Off. .

OTHER PUBLICATIONS

"Chemical Abstracts" vol. 101, 1984 54508u.

Primary Examiner—Alan Sigel
Attorney, Agent, or Firm—Birch, Stewart, Kolasch & Birch

[57] ABSTRACT

1,1,1,4,4,4-Hexafluorobutane is prepared by reducing 2-chloro-1,1,1,4,4,4-hexafluorobutene-2 with hydrogen in the presence of a hydrogenation catalyst containing an alloy which contains at least one first metal component selected from the group consisting of platinum and palladium and at least one second metal component selected from the group consisting of silver, copper, gold, tellurium, zinc, chromium, molybdenum and thallium. 1,1,1,4,4,4-Hexafluorobutane can be prepared in a high selectivity and a high yield.

15 Claims, No Drawings

PREPARATION OF 1,1,1,4,4,4-HEXAFLUOROBUTANE

FIELD OF THE INVENTION

The present invention relates to a method for preparing 1,1,1,4,4,4-hexafluorobutane.

RELATED ART 1,1,1,4,4,4-Hexafluorobutane is s compound useful as a refrigerant carrier, a foaming agent and a solvent. As a method for preparing 1,1,1,4,4,4-hexafluorobutane, a method is known which comprises hydrogenating 2-chloro-1,1,1,4,4,4-hexafluorobutene-2 or 1,1,1,4,4,4-hexafluorobutene-2 in a liquid phase in the presence of various noble metal catalyst. However, such method is not commercially suitable, since a by-product is produced in a large amount so that the yield is low.

A method which comprises hydrogenating 1,1,1,4,4,4-hexafluorobutyne-2 in the presence of a palladium catalyst is also known (Youji Huaxue, 2, 125 (1985)). However, this method requires a raw material which cannot be easily produced and is not commercially preferable method.

PROBLEM TO BE SOLVED BY THE INVENTION

An object of the present invention is to provide a method for preparing 1,1,1,4,4,4,-hexafluorobutane in a gas phase by a hydrogen reduction without the above problems.

MEANS FOR SOLVING THE PROBLEM

The inventors have intensively studied to develop an easy method for commercially preparing 1,1,1,4,4,4-hexafluorobutane in a high yield, and found that 1,1,1,4,4,4-hexafluorobutane can be obtained with good selectivity and a high yield when 2-chloro-1,1,1,4,4,4-hexafluorobutene-2 is used as a raw material and is hydrogenated in a gas phase in the presence of an alloy catalyst containing platinum or palladium, thus completed the present invention.

The gist of the present invention resides in a method for preparing 1,1,1,4,4,4-hexafluorobutane comprising reducing 2-chloro-1,1,1,4,4,4-hexafluorobutene-2 with hydrogen in the presence of a hydrogenation catalyst comprising an alloy which comprises at lease one first metal component selected from the group consisting of platinum and palladium and at lease one second metal component selected from the group consisting of silver, copper, gold, tellurium, zinc, chromium, molybdenum and thallium.

In the present invention, the hydrogenation catalyst contains the alloy comprising the first metal component and the second metal component, which alloy is an active component of the catalyst.

It is generally known that, in the alloy catalyst, a property of the component element is exhibited according to an alloy composition. In the present invention, an amount of the second metal component is suitably from 0.01 to 500 parts by weight, particularly from 0.1 to 300 parts by weight per 100 parts by weight of the first metal component in view of the utilization of the property of platinum and palladium.

A suitable carrier of the hydrogenation catalyst is, for example, active carbon, alumina, zirconia and titania. While a content of the alloy supported on the carrier in the catalyst may be from 0.05 to 5% by weight, a preferable content is from 0.5 to 2% by weight. The particle size of the carrier gives no strong effect on the reaction, and it is preferably from 0.01 to 100 mm.

A ratio of 2-chloro-1,1,1,4,4,4-hexafluorobutene-2 (R-1326) to hydrogen in the hydrogenation reaction can be widely varied. However, at least a stoichiometric amount of hydrogen (namely, at lease 2 mol of hydrogen per 1 mol of R-1326) is usually used so that the hydrogenation reaction is conducted and a chlorine atom is eliminated. The amount of hydrogen may be relatively larger than the stoichiometric amount, for example at least 4 mol per 1 mol of R-1326.

A reaction mode is a gas phase reaction in which a gaseous R-1326 and hydrogen are passed in contact with the hydrogenation catalyst filled in a reactor tube. A gas phase reaction may be a fixed bed gas phase reaction, a fluidized bed gas phase reaction or the like.

The reaction pressure is not limited and may be any of an increased pressure, a decreased pressure and an atmospheric pressure. The reaction is preferably conducted under increased pressure or atmospheric pressure, since the reduced pressure requires a complex apparatus.

The reaction temperature is usually from 0° to 450° C., preferably from 50° to 300° C.

The contacting time is usually from 0.1 to 300 seconds, preferably from 1 to 30 seconds.

R-1326 can be prepared by any of suitable methods. A preferable method for preparing R-1326 comprises fluorinating hexachloro-1,3-butadiene in a liquid phase in the presence of antimony chloro-fluoride and hydrogen fluoride. This method gives R-1326 in a low cost at a high yield in an easy manner.

It is economically advantageous to use hexachloro-1,3-butadiene as a raw material. Compounds prepared by conducting an addition reaction of hydrogen chloride or hydrogen fluoride with hexachloro-1,3-butadiene can also be used.

These compounds are intermediates of the reaction or equivalent compounds, and these compounds and mixtures thereof can be used as the raw material. However, since the addition reaction cf hydrogen fluoride with hexachloro-1,3-butadiene and a fluorination reaction of the adduct proceed successively, these reactions may be conducted as continuous reactions.

It is known that antimony pentachloride added to a reaction system is partially fluorinated in the presence of hydrogen fluoride to give $SbCl_xF_y$ (wherein x and y are the numbers which satisfy $x+y=5$). In the case that it is used as a catalyst for fluorinating a compound having a double bond or a hydrogen atom which can be chlorinated, such as hexachloro-1,3-butadiene, when the fluorine content is larger, the fluorination reaction proceeds more rapidly so as to prevent the generation of a chlorinated product which is a by-product. The presence of hydrogen fluoride in excess of the amount of added antimony pentafluoride gives a high fluorine content of $SbCl_xF_y$ and accelerates the addition reaction so that R-1326 can be prepared with good selectivity.

The amount cf hydrogen fluoride added in the reactor is an amount of consumed hydrogen fluoride plus an amount of hydrogen fluoride which escapes together with the product.

Thus, the amount of hydrogen fluoride in the reaction system can be maintained at a constant level. However, the amount of hydrogen fluoride may vary within a range accepted by the reactor volume, insofar as the excess amount of hydrogen fluoride can be maintained.

The necessary whole amount of hydrogen fluoride can be charged into the reactor before conducting the reaction.

The amount of hexachloro-1,3-butadiene charged in the reactor is advantageously small based on an amount of antimony pentachloride added no the reaction system. When the amount of hexachloro-1,3-butadiene is too small, the amount of product is disadvantageously small.

When the amount of hexachloro-1,3-butadiene is too large, the selectivity is low while the reaction proceeds.

The amount of supplied hexachloro-1,3-butadiene is between 2 mol/hr and 100 mol/hr based on 1 mol of charged antimony pentachloride. An amount between 5 mol/hr and 50 mol/hr is preferable. The reaction proceeds at a temperature of 40° C., and in this case, the selectivity decreases unless an amount of hexachloro-1,3-butadiene based on charged $SbCl_5$ is small. A high reaction temperature is advantageous in the productivity and the selectivity, and the reaction pressure must be high depending on the reaction temperature.

Since the high reaction pressure increases the cost of apparatus, the reaction is preferably practically conducted at a temperature between 50° C. and 150° C.

The reaction pressure is increased depending on the reaction temperature and is preferably from 3 $kg/cm^2$ to 30 $kg/cm^2$ so as to separate the product from hydrogen fluoride. In this reaction, a method may be used in which only HCl which is generated by the reaction is removed from the reaction system under the high pressure so that the R-1326 product is accumulated in the reaction system.

While a large amount of hydrogen fluoride present together with $SbCl_xF_y$ gives no effect on the reaction, it decreases the productivity per unit reactor volume. When the amount of hydrogen fluoride is small, the selectivity decreases while the reaction proceeds. In order to prevent the above, the amount of supplied hexachloro-1,3-butadiene must be small.

Practically, the amount of hydrogen fluoride is between 5 mol and 500 mol per 1 mol of antimony pentachloride. The amount between 50 mol and 200 mol is preferable.

In a preferred embodiment, hydrogen fluoride and hexachloro-1,3-butadiene raw material are charged in the reaction system while maintaining a constant reaction pressure and the produced R-1326 is removed.

R-1326 containing impurities prepared by the above method may be subjected to the hydrogenation reaction without or after purifying R-1326.

PREFERRED EMBODIMENTS OF THE INVENTION

The present invention is illustrated by following Examples which do not limit the present invention.

Preparative Example 1

In a 500 ml Hastelloy autoclave equipped with a condenser, $SbCl_5$ (29.9 g, 0.1 mol) was charged and cooled. Hydrogen fluoride (100 g, 5 mol) was added. Then, the temperature was gradually increased and the reaction was conducted at 80° C. for 3 hours. Hexachloro-1,3-butadiene (0.5 mol/hr) and hydrogen fluoride (6 mol/hr) were added at 80° C.

The reaction pressure was kept at from 8 $kg/cm^2$ to 11 $kg/cm^2$ so that a reactor weight was constant. An evolved gas was washed with water and trapped with a dry ice trap. When 520 g (2 mol) of hexachloro-1,3-butadiene was added, the reaction was discontinued. R-1326 (376 g, yield: 87%) was obtained as the reaction product. It was confirmed by GLC that 97% of the product was the object product R-1326. A by-product other than an intermediate was not present in the reactor.

Preparative Example 2

In a 500 ml Hastelloy autoclave equipped with a condenser, $SbCl_5$ (29.9 g, 0.1 mol) was charged and cooled. Hydrogen fluoride (300 g, 15 mol) was added. Then, the temperature was gradually increased and the reaction was conducted at 80° C. for 3 hours. Hexachloro-1,3-butadiene (0.5 mol/hr) was added at 80° C.

The reaction pressure was kept at from 8 $kg/cm^2$ to 11 $kg/cm^2$. An evolved gas was washed with water and trapped with a dry ice trap. When 260 g (1 mol) of Hexachloro-1,3-butadiene was added, the reaction was discontinued. The reaction product (185 g, yield: 86%) was obtained. It was confirmed by GLC that 98.5% of the product was the object product R-1326. A by-product other than an intermediate was not present in the reactor.

Preparative Example 3

In a 500 ml Hastelloy autoclave equipped with a condenser, $SbCl_5$ (29.9 g, 0.1 mol) was charged and cooled. Hydrogen fluoride (50 g, 2.5 mol) was added. Then, the temperature was gradually increased and the reaction was conducted at 80° C. for 3 hours. Hexachloro-1,3-butadiene (0.5 mol/hr) and hydrogen fluoride (3 mol/hr) were added at 80° C. The reaction pressure was kept at from 12 $kg/cm^2$ to 15 $kg/cm^2$. An evolved gas was washed with water and trapped with a dry ice trap. When 260 g (1 mol) of Hexachloro-1,3-butadiene was added, the reaction was discontinued. A combined weight of the product in the reactor and the product in the Trap was 190 g (yield: 88%). It was confirmed by GLC than 99% of the product was the object product R-1326. A by-product other than an intermediate was not present in the reactor.

EXAMPLE 1

To a platinum catalyst containing platinum in a content of 0.5% on active carbon, an aqueous solution of $CuCl_2$ in an amount of 0.1% based on the active carbon weight was added. Formalin (0.2 ml) was dropwise added and the mixture was aged at 50° C. for 5 hours. Then, water was distilled off at a reduced pressure and the residue was dried at 100° C. for one day.

The resultant catalyst (16 cc) was filled in a SUS-316 reactor tube having an inner diameter of 2 cm and a length of 40 cm. The reactor tube was heated at 110° C. in an electric furnace with flowing a nitrogen gas in the reactor tube. After the temperature of the reactor tube reached the desired temperature, the flow of the nitrogen gas was discontinued and previously vaporized 2-chloro-1,1,1,4,4,4-hexafluorobutene-2 (21 cc/min) and hydrogen (43 cc/min) were supplied. The reaction temperature was 110° C. The resultant gas was washed with water, dried with calcium chloride and then analyzed with a gas chromatography. The results are shown in Table 1.

EXAMPLE 2

In the same manner as in Example 1, an alloy catalyst which contains 0.1% of silver was obtained except that AgNO$_3$ was added to the platinum catalyst containing 0.5% of platinum on active carbon, and then the reaction was conducted. The results are shown in Table 1.

EXAMPLE 3

In the same manner as in Example 1, an alloy catalyst which contains 0.1% of tellurium was obtained except that TeCl$_2$ was added to the platinum catalyst containing 0.5% of platinum on active carbon, and then the reaction was conducted. The results are shown in Table 1.

EXAMPLE 4

In the same manner as in Example 1, an alloy catalyst which contains 0.1% of gold was obtained except that AuCl$_3$ was added to the platinum catalyst containing 0.5% of platinum on active carbon, and then the reaction was conducted. The results are shown in Table 1.

EXAMPLE 5

In the same manner as in Example 1, an alloy catalyst which contains 2% of zinc was obtained except that ZnCl$_2$ was added to the platinum catalyst containing 0.5% of platinum on active carbon. The alloy catalyst (16 cc) was filled in a SUS-316 reactor tube having an inner diameter of 2 cm and a length of 40 cm. The reactor tube was heated at 110° C. in an electric furnace with flowing a nitrogen gas in the reactor tube. After the temperature of the reactor tube reached the desired temperature, the flow of the nitrogen gas was discontinued and previously vaporized 2-chloro-1,1,1,4,4,4-hexafluorobutene-2 (33 cc/min) and hydrogen (66 cc/min) were supplied. The reaction temperature was 110° C. The resultant gas was washed with water, dried with calcium chloride and then analyzed with a gas chromatography. The results are shown in Table 1.

EXAMPLE 6

In the same manner as in Example 1, an alloy catalyst which contains 2% of chromium was obtained except that Cr(NO$_3$)$_3$•9H$_2$O was added to the platinum catalyst containing 0.5% of platinum on active carbon. The alloy catalyst (16 cc) was filled in a SUS-316 reactor tube having an inner diameter of 2 cm and a length of 40 cm. The reactor tube was heated at 130° C. in an electric furnace with flowing a nitrogen gas in the reactor tube. After the temperature of the reactor tube reached the desired temperature, the flow of the nitrogen gas was discontinued and previously vaporized 2-chloro-1,1,1,4,4,4-hexafluorobutene-2 (24.6 cc/min) and hydrogen (73.8 cc/min) were supplied. The reaction temperature was 130° C. The resultant gas was washed with water, dried with calcium chloride and then analyzed with a gas chromatography. The results are shown in Table 1.

EXAMPLE 7

In the same manner as in Example 1, an alloy catalyst which contains 2% of thallium was obtained except that TlCl$_3$ was added to the platinum catalyst containing 0.5% of platinum on active carbon. The alloy catalyst (16 cc) was filled in a SUS-316 reactor tube having an inner diameter of 2 cm and a length of 40 cm. The reactor tube was heated at 130° C. in an electric furnace with flowing a nitrogen gas in the reactor tube. After the temperature of the reactor tube reached the desired temperature, the flow of the nitrogen gas was discontinued and previously vaporized 2-chloro-1,1,1,4,4,4-hexafluorobutene-2 (27.6 cc/min) and hydrogen (55.1 cc/min) were supplied. The reaction temperature was 130° C. The resultant gas was washed with water, dried with calcium chloride and then analyzed with a gas chromatography. The results are shown in Table 1.

EXAMPLE 8

In the same manner as in Example 1, an alloy catalyst which contains 2% of molybdenum was obtained except that (NH$_4$)$_6$Mo$_7$O$_{24}$•4H$_2$O was added to the platinum catalyst containing 0.5% of platinum on active carbon. The alloy catalyst (14.5 cc) was filled in a SUS-316 reactor tube having an inner diameter of 2 cm and a length of 40 cm. The reactor tube was heated at 200° C. in an electric furnace with flowing a nitrogen gas in the reactor tube. After the temperature of the reactor tube reached the desired temperature, the flow of the nitrogen gas was discontinued and previously vaporized 2-chloro-1,1,1,4,4,4-hexafluorobutene-2 (22 cc/min) and hydrogen (44 cc/min) were supplied. The reaction temperature was 200° C. The resultant gas was washed with water, dried with calcium chloride and then analyzed with a gas chromatography. The results are shown in Table 1.

TABLE 1

| Example No. | Conversion (%) | Selectivity (%) |
| --- | --- | --- |
| 1 | 98 | 96 |
| 2 | 99 | 98 |
| 3 | 99 | 95 |
| 4 | 97 | 96 |
| 5 | 98 | 93 |
| 6 | 99 | 95 |
| 7 | 97 | 93 |
| 8 | 97 | 94 |

What is claimed is:

1. A method for preparing 1,1,1,4,4,4-hexafluorobutane comprising reducing 2-chloro-1,1,1,4,4,4-hexafluorobutene-2 with hydrogen in the presence of a hydrogenation catalyst comprising an alloy which comprises at least one first metal component selected from the group consisting of platinum and palladium and at least one second metal component selected from the group consisting of silver, gold, tellurium, zinc, chromium, molybdenum and thallium.

2. The method according to claim 1, wherein 2-chloro-1,1,1,4,4,4-hexafluorobutene-2 is prepared by fluorinating hexachloro-1,3-butadiene in a liquid phase in the presence of antimony chloro-fluoride and hydrogen fluoride.

3. The method according to claim 1, wherein said first metal component is platinum.

4. The method according to claim 3, wherein said second metal component is silver.

5. The method according to claim 3, wherein said second metal component is tellurium.

6. The method according to claim 3, wherein said second metal component is gold.

7. The method according to claim 3, wherein said second metal component is zinc.

8. The method according to claim 3, wherein said second metal component is chromium.

9. The method according to claim 3, wherein said second metal component is thallium.

10. The method according to claim 3, wherein said second metal component is molybdenum.

11. The method according to claim 1, wherein said alloy comprises 0.01 to 500 parts by weight of said second metal component per 100 parts by weight of said first metal component.

12. The method according to claim 11, wherein said alloy is present at a concentration of 0.05 to 5% by weight of a carrier for said catalyst.

13. The method according to claim 1, wherein the molar ratio of hydrogen to 2-chloro-1,1,1,4,4,4-hexafluorobutene-2 is 2:1 or greater.

14. The method according to claim 13, wherein the molar ratio of hydrogen to 2-chloro-1,1,1,4,4,4-hexafluorobutene-2 is 2:1.

15. The method according to claim 2, wherein said fluorination is conducted at a reaction temperature between 50° and 150° C. and at a constant reaction pressure between 3 and 30 kg/cm$^2$.

* * * * *